US009686993B2

(12) United States Patent
Buschhaus

(10) Patent No.: US 9,686,993 B2
(45) Date of Patent: Jun. 27, 2017

(54) METHOD FOR INHIBITING MYCOTOXIN PRODUCTION

(75) Inventor: Herbert Buschhaus, Ratingen (DE)

(73) Assignee: Nippon Soda Co., Ltd., Tokyo (JP)

( * ) Notice: Subject to any disclaimer, the term of this patent is extended or adjusted under 35 U.S.C. 154(b) by 2243 days.

(21) Appl. No.: 11/909,888

(22) PCT Filed: Mar. 29, 2006

(86) PCT No.: PCT/JP2006/306487
§ 371 (c)(1),
(2), (4) Date: Sep. 27, 2007

(87) PCT Pub. No.: WO2006/106742
PCT Pub. Date: Oct. 12, 2006

(65) Prior Publication Data
US 2009/0270471 A1    Oct. 29, 2009

(30) Foreign Application Priority Data

Mar. 31, 2005    (JP) ................................ 2005-102646

(51) Int. Cl.
A01N 43/653    (2006.01)
C07D 249/08    (2006.01)
A01P 3/00    (2006.01)
A01N 47/34    (2006.01)

(52) U.S. Cl.
CPC .................................... A01N 47/34 (2013.01)

(58) Field of Classification Search
USPC ................................ 514/183, 383; 548/267.8
See application file for complete search history.

(56) References Cited

U.S. PATENT DOCUMENTS

| | | | |
|---|---|---|---|
| 3,929,448 | A | 12/1975 | Brantley |
| 4,447,984 | A | 5/1984 | Sampson et al. |
| 5,326,777 | A | 7/1994 | Ludwig et al. |
| 5,597,840 | A | 1/1997 | Moore |
| 6,319,949 | B1 | 11/2001 | Schussler et al. |
| 2005/0215764 | A1* | 9/2005 | Tuszynski et al. ........... 530/358 |
| 2005/0222051 | A1 | 10/2005 | Andersch et al. |

FOREIGN PATENT DOCUMENTS

| | | |
|---|---|---|
| EG | 1987020085 | 2/1987 |
| EP | 1 319 341 | 6/2003 |
| JP | 5-201806 | 8/1993 |
| JP | 2001-72512 | 3/2001 |
| JP | 2002-526053 | 8/2002 |
| JP | 2002-540787 | 12/2002 |
| JP | 2003-300804 | 10/2003 |
| JP | 2002-533057 | 10/2005 |
| WO | WO 99/58689 | 11/1999 |
| WO | WO 00/16632 | 3/2000 |
| WO | WO 00/60061 | 10/2000 |
| WO | WO 03/063592 | 8/2003 |

OTHER PUBLICATIONS

Cromey (Effects of Fungicides Applied at Anthesis on Fusarium Head Blight and Mycotoxins in Wheat, Arable Entomology and Pathology, New Zealand Plant Protection 55:341-346(2002).*
Food and Environment Protection Act, 1986, Part III Thiophanate-Methyl, Control of Pesticides Regulations 1986, Evaluation of Fully Approved or Provisionally Approved Products (1992), printed pp. 1-170.*
Japanese Patent Office, International Search Report, dated May 23, 2006, from related International Patent Application No. PCT/JP2006/306487, filed Mar. 29, 2006.
Cromey et al., "Effects of fungicides applied at anthesis on fusarisum head blight and mycotoxins in wheat," *Proceedings of the New Zealand Plant Protection Conference* (2002), 55$^{th}$, 341-346.
Ueda et al., "Effects of thiophanate methyl on the incidence of scan and the mycotoxin contamination in wheat and barley," *Ann. Phytopath Soc. Japan*, (1988), 54, 476-482, (English-language abstract included).
Vanova et al., "Effect of spring barley protection on the production of *fusarium* spp. mycotoxins in grain and malt using fungicides in field trials," *Plant Soil Environ.*, (2004), 50(10), 447-455.
Siranidou et al., "Chemical control of fusarium head blight on wheat," *J. Plant Diseases and Protection*, (2001), 108(3), 231-243.
Buschhaus, "A fungicide application system for control of fusarium disease and minimization of quality decrease in wheat," *Modern Fungicides and Antifungal Compounds II*, May 24-29, 1998, (1999), 267-272.
Milus et al., "Evaluation of foliar fungicides for controlling fusarium head blight of wheat," *Plant Disease*, (1994), 78(7), 697-699.
Hicks et al., "Need to determine the relative developmental risks of fusarium mycotoxin dexoynivalenol (DON) and benomyl (BEN) in wheat," *Human and Ecological Risk Assessment*, (2000), 6(2), 341-354.
Tjamos et al., "Aspergillus niger and aspergillus carbonarius in corinth raisin and wine-producing vineyards in Greece: Population composition, Ochratoxin A production and chemical control," *J. Phytopathology*, (2004), 152, 250-255.
D'Mello et al., "Pesticide use and mycotoxin production in fusarium and aspergillus phytopathogens," *European Journal of Plant Pathology*, (1998), 104, 741-751.

(Continued)

*Primary Examiner* — Kathrien Cruz
(74) *Attorney, Agent, or Firm* — Foley & Lardner LLP

(57) ABSTRACT

The present invention provides a method for prominently inhibiting the production in fungi of mycotoxin, which has serious effects on health of humans and other animals, and provides a mycotoxin production inhibitor. Mycotoxin content such as deoxinivalenol (DON) in harvested crops can be reduced without a correlation with the control effects against fungi by spraying a fungicide containing a benzimidazole-type fungicidal compound such as thiophanate-methyl as an active ingredient onto food crops such as wheat, barley, and the like. Concomitant use of the benzimidazole-type fungicidal compound and a sterol biosynthesis inhibitor (SBI agent) such as tebuconazole can further enhance the effect.

4 Claims, 1 Drawing Sheet

(56) References Cited

OTHER PUBLICATIONS

Japanese Office Action with English-language translation, Japanese Patent Application No. 2007-512796, mailed Aug. 3, 2010.
"Fusarium Head Blight of Wheat in Hokkaido," Agchem Age, vol. No. 185, pp. 22 to 27 (partial English-language translation provided).
"Prevention of Fusarium Head Blight of Wheat and Barley," Agchem Age, vol. No. 185, pp. 31 to 34 (English-language translation provided).
Japanese Office Action for JP Application No. 2007-512796, mailed on Jul. 3, 2012, 6 pages (with English translation).
Yoshizawa, Takumi, et al., "Inhibition of Trichothecenes Production by Thiophanate-methyl Fungicide and Its Metabolite", J. Antibact. Antifung. Agents, 1992, vol. 20, No. 5, pp. 247-250 (with English translation).
Agchem Age, 2003, No. 185, pp. 28-30 (with English translation).
Edwards, "Influence of Agricultural Practices on Fusarium Infection of Cereals and Subsequent Contamination of Grain by Trichothecene Mycotoxins," Oct. 10, 2004, Toxicology Letters, Elsevier Biomedical Press, Amsterdam, NL, vol. 153, No. 1, XP004549273, pp. 29-35.
Hassan, "Phytotoxicity of Pathogenic Fungi and their Mycotoxins to Cereal Seedling Viability," May 1, 2000, Mycopathologia, Kluwer Academic Publishers, vol. 148, No. 3, XP019259523, pp. 149-155.
EP Communication including Supplementary European Search Report from EP Appln. No. 06730435.2, Oct. 8, 2012, 9 pages.
Jones R. K. et al., "Evaluation of Benomyl and Triazole in Reducing AFLA Toxin B-1 Concentrations in Field Corn ZEA-MAYS," Aug. 8, 1982, Phytopathology, vol. 72, No. 7, XP001538549, p. 970.
Gabal et al., "Preliminary Study on the use of Thiabendazole in the Control of Common Toxigenic Fungi in Grain Feed," Jun. 1, 1987, Veterinary and human Toxicology, Manhattan, US, vol. 29, No. 3, XP009133565, pp. 217-221.
Chala et al., "An Integrated Approach to the Evaluation of the Efficacy of Fungicides Against Fusarium Culmorum, the Cause of Head Blight of Wheat," Jan. 1, 2003, Journal of Phytopathology-Phytopathologische Zeitschrift, Wiley-Blackwell Verlag GmbH, DE, XP002357495, pp. 673-678.
Edwards et al., "Quantification of Trichothecene-Producing *Fusarium* Species in Harvested Grain by Competitive PCR to determine Efficacies of Fungicides Against Fusarium Head Blight of Winter Wheat," Apr. 1, 2001, Applied and Environmental Microbiology, US, vol. 67, No. 4, XP001076826, pp. 1575-1580.
Japanese Office Action for JP Applicaton No. 2011-021003, mailed on May 13, 2014, 14 pages (with English translation).
Hatsuo Saitoh [National Institute of Agrobiological Sciences], MAFF Microorganism Genetic Resources Manual No. 25 (2009), 19 pages (with partial translation).
Office Action,, Indian Patent Application No. 3636/KOLNP/2007, mailed Oct. 21, 2010.
"Entrusted Tests", 2002, pp. 31-32, edited by Japan Plant Protection Association (with partial English translation).
Declaration of Sakiko Sugihara declaring English translation of document 1 is accurate.
R. K. Jones, "Assessments of Fusarium Head Blight of Wheat and Barley in Response to Fungicide Treatment," *Plant Disease*, Sep. 2000, vol. 84, No. 9, pp. 1021-1030.
Notification of the First Office Action, Chinese Application No. 200680009647.4, dated Feb. 5, 2010 (English-language translation provided).
English-language translation of Egyptian Office Action, Egyptian Patent Application No. 1018/2007 issued May 22, 2010.

\* cited by examiner

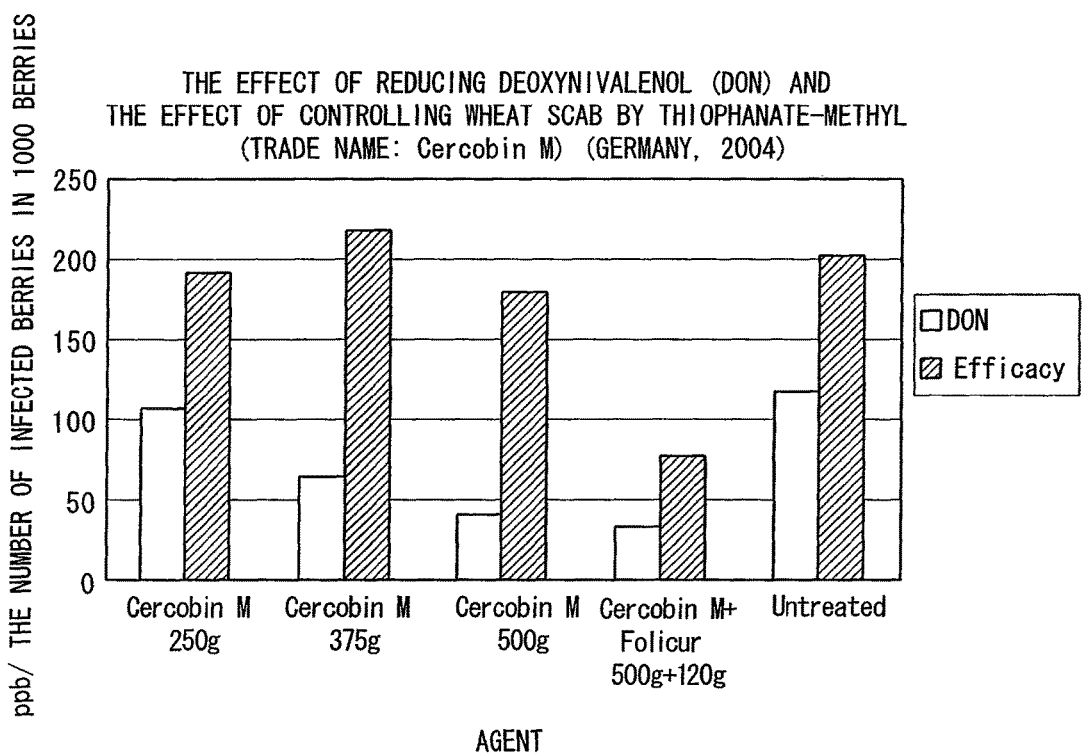

METHOD FOR INHIBITING MYCOTOXIN PRODUCTION

This application is a national phase filing (35 U.S.C. §371) OF PCT/JP2006/306487, filed on Mar. 29, 2006, which claims priority under 35 U.S.C. §119 from Japanese application number JP 2005 102646, filed Mar. 31, 2005.

TECHNICAL FIELD

The present invention relates to a method for inhibiting mycotoxin production in fungi and to a mycotoxin production inhibitor and the like. More specifically, the present invention relates to a method for inhibiting mycotoxin production in fungi wherein the mycotoxin content in harvested crops is reduced by spraying a benzimidazole-type fungicidal compound onto food crops and to a mycotoxin production inhibitor containing the benzimidazole-type fungicidal compound as an active ingredient.

BACKGROUND ART

Mycotoxin, which is formed by fungi, is known to have serious effects on the health of humans and animals as follows: developing symptoms of poisoning such as diarrhea or nausea, causing cancer, and having the possibility to trigger premature births or abortion. Therefore, it has been a long-standing task to find how to inhibit mycotoxin production in fungi which infect food crops. Particularly, a problem has arisen recently in that infection of food crops with fungi during their growth cycle causes exposure of the harvested crops to mycotoxin, with the result that the harvested crops can not be provided as food.

In order to prevent the aforementioned problem, some measures have been taken: improving growth conditions of plants, avoiding crop rotation, improving strain, and transforming plants so as to provide resistance to mycotoxin (see, for example patent documents 1 and 2). In addition, various types of fungicide are applied to food crops to prevent them from becoming infected with fungi.

[Patent Document 1] Domestic re-publication of PCT international publication for patent application No. 2002-540787.

[Patent Document 2] Domestic re-publication of PCT international publication for patent application No. 2002-533057.

DISCLOSURE OF THE INVENTION

The task of the present invention is to provide a method for inhibiting mycotoxin production prominently, since mycotoxin is formed by fungi and it has serious effects on the health of humans and other animals, and to provide a mycotoxin production inhibitor.

The present inventor found that a benzimidazole-type fungicidal compound such as thiophanate-methyl inhibits mycotoxin production in harvested crops without a correlation with the fungicidal effect in the process of spraying a wide variety of fungicides onto food crops for study in order to solve the above-mentioned problems, which leads to completion of the present invention.

The present invention relates to (1) a method for inhibiting mycotoxin production, wherein the mycotoxin content in harvested crops is reduced by spraying a fungicide containing a benzimidazole-type fungicidal compound as an active ingredient onto food crops; (2) the method for inhibiting mycotoxin production according to (1), wherein the fungicide is sprayed onto food crops during the period from their anthesis stage until their harvest; (3) the method for inhibiting mycotoxin production according to (1) or (2), wherein the mycotoxin content in harvested crops is reduced without a correlation with the control effect against fungi by spraying a fungicide containing a benzimidazole-type fungicidal compound as an active ingredient onto food crops; (4) the method for inhibiting mycotoxin production according to any one of (1) to (3), wherein the fungicide is an admixture containing the benzimidazole-type fungicide and any one of the following: a sterol biosynthesis inhibitor, a strobilurin-type agent, and a guanidine-type fungicide; (5) the method for inhibiting mycotoxin production according to any one of (1) to (4), wherein the benzimidazole-type fungicide is a thiophanate-methyl agent; and (6) the method for inhibiting mycotoxin production according to any one of (1) to (5), wherein the food crop is wheat, barley, and the like.

The present invention further relates to (7) a mycotoxin production inhibitor for mycotoxin in harvested crops, which is a fungicide containing a benzimidazole-type fungicidal compound as an active ingredient; (8) the mycotoxin production inhibitor according to (7), wherein the fungicide is an admixture containing the benzimidazole-type fungicide and any one of the following: a sterol biosynthesis inhibitor, a strobilurin-type agent, and a guanidine-type fungicide; (9) the mycotoxin production inhibitor according to (7) or (8), wherein the benzimidazole-type fungicide is a thiophanate-methyl agent; (10) the mycotoxin production inhibitor according to any one of (7) to (9), wherein the crop is wheat, barley, and the like; (11) use of the benzimidazole-type fungicide for reducing the mycotoxin content in harvested crops; and (12) an agrichemical wherein an indication is displayed that the benzimidazole-type fungicide is used for inhibiting mycotoxin production in harvested crops.

Production of mycotoxin, which is a harmful substance formed by fungi, is inhibited by the present invention, leading to provision of extremely safe crops, even if fungi control is incomplete.

BRIEF DESCRIPTION OF THE DRAWINGS

The FIGURE The effect of controlling wheat scab brought about by spraying thiophanate-methyl (trade name: Cercobin M), and the result of measuring the content of deoxinivalenol (DON), which is a mycotoxin.

BEST MODE FOR CARRYING OUT THE INVENTION

As for the method for inhibiting mycotoxin production of the present invention, it is not specifically limited as long as it is a method for inhibiting mycotoxin production wherein the mycotoxin content in harvested crops is reduced by spraying a benzimidazole-type fungicidal compound onto food crops, particularly onto wheat, barley, and the like, or a method for inhibiting mycotoxin production wherein the mycotoxin content in harvested crops is reduced by spraying an admixture containing a benzimidazole-type fungicidal compound and any one of the following: a sterol biosynthesis inhibitor, a strobilurin-type agent, and a guanidine-type fungicide onto food crops. Further, it is a method for inhibiting mycotoxin production wherein the benzimidazole-type fungicidal compound of the present invention is sprayed onto food crops during the period from their anthesis stage until their harvest. In addition, the present invention reduces the mycotoxin content in harvested crops without a correlation with the control effect against fungi by spraying a benzimidazole-type fungicide onto food crops. As for a mycotoxin production inhibitor, there is no specific limitation as long as it comprises the benzimidazole-type fungicidal compound as an active ingredient or it comprises an admixture containing the benzimidazole-type fungicidal compound and any one of the following: a sterol biosynthesis inhibitor, a strobilurin-type agent, and a guanidine-type fungicide, as an active ingredient. Mycotoxin is a harmful substance formed by fungi, and trichothecene, ergoalkaloid, fumonisin, zearalenone, ochratoxin mycotoxins and the like can be specifically exemplified. Among them, deoxynivalenol (DON), one type of trichothecene can be preferably exemplified, whose contamination of grain has emerged as a particular problem.

Mycotoxin is usually formed by fungi which infect food crops, specifically by *fusarium, penicillium, aspergillus* and so on. Hence, a problem has arisen that mycotoxin contaminates wheat, barley, and the like due to wheat scab (fusarium). Meanwhile, the mycotoxin content in harvested crops can be quantified using an ELISA method, HPLC method, gas chromatography method and the like.

As for the aforementioned benzimidazole-type fungicide, benomyl, carbendazine, fubendazole, cypendazole, thiophanate-methyl, and thiophanate can be specifically exemplified, among these a thiophanate-methyl agent (trade names: Topsin M, Cercobin M) can be preferably exemplified. These benzimidazole-type fungicides can be used as a single agent or in combination of two or more agents. The used benzimidazole-type fungicide can be applied not only in pure form without adding other constituents in actual use, but also in a form that can be used as a general agrichemical, i.e. a water-dispersible powder, particle, powder, suspension, granulated water-dispersible powder, and the like for the purpose of its use as an agrichemical.

As for the aforementioned sterol biosynthesis inhibitor (SBI), the following can be specifically exemplified; tebuconazole, triadimefon, triadimenol, bitertanol, myclobutanil, hexaconazole, propiconazole, triflumizole, prochloraz, peflirazoate, fenarimol, pyrifenox, triforine, flusilazole, ethaconazole, dichlobutrazol, fluotrimazol, flutriafen, penconazole, diniconazole, imazalil, tridemorph, fenpropimorph, buthiobate, epoxiconazole, metoconazole, fluquinconazole, prochloraz and protioconazol, while tebuconazole can preferably be exemplified among these. Concomitant use of one or more of these SBI agents and the benzimidazole-type fungicide can enhance the inhibitory action of the benzimidazole-type fungicide against mycotoxin production.

In addition, the benzimidazole-type fungicide can be used as a single agent; it can be used concomitantly with one or more of the other agrichemicals such as various fungicides, pesticides, acaricides, nematicides, and plant growth regulators, as well as being used concomitantly with SBI agents as described above. Concomitant use of these agrichemicals and the benzimidazole-type fungicide, or concomitant use of these agrichemicals, the benzimidazole-type fungicide, and SBI agents enables control against fungi, acari, and so on as well as inhibition of mycotoxin production. Further, concomitant use of the benzimidazole-type fungicidal compound and a strobilurin-type compound, or concomitant use of the benzimidazole-type fungicidal compound and a guanidine-type fungicide can advantageously inhibit mycotoxin production.

As for the aforementioned fungicide, the following can be specifically exemplified: copper fungicide such as basic copper chloride and basic copper sulfate, sulfur fungicide such as thiuram, zineb, maneb, mancozeb, ziram, propineb, and polycarbamate, polyhaloalkylthio fungicide such as captan, folpet, dichlorfluanid, organochlorine fungicide such as chlorothalonil, fthalide, organophosphorous fungicide such as IBP, EDDP, tolclophos-methyl, pyrazophos, fosetyl, dicarboxyimide fungicide such as iprodione, procymidone, vinclozolin, fluoromide, carboxyamide fungicide such as oxycarboxin, mepronil, flutolanil, tecloftalam, trichlamide, pencycuron, acylalanine fungicide such as metalaxyl, oxadixyl, furalaxyl, methoxyacrylate fungicide such as kresoxim-methyl (stroby), azoxystrobin, metominostrobin, trifloxystrobin, pyraclostrobin, anilinopyrimidine fungicide such as andupurine, mepanipyrim, pyrimethanil, cyprodinil, antibiotic agents such as polyoxin, blasticidin S, kasugamycin, validamycine, dihydrostreptomycin sulfate, and the like.

Other than those above, the following fungicides can be used concomitantly; propamocarb hydrochloride, quintozene, hydroxyisoxazole, methasulfocarb, anilazine, isoprothiolane, probenazole, chinomethionat, dithianon, dinocap, diclomezine, ferimzone, fluazinam, pyroquilon, tricyclazole, oxolinic acid, iminoctadine acetate, iminoctadine albesilate, cymoxanil, pyrrolnitrin, diethofencarb, binapacryl, lecithin, sodium bicarbonate, fenaminosulf, dodine, dimethomorph, phenazine oxide, carpropamid, flusulfamide, fludioxonil, famoxadone, and the like.

As for the aforementioned pesticides, the following can be exemplified: organophosphorous pesiticides and carbamate pesticides such as fenthion, fenitrothion, diazinon, chlorpyrifos, ESP, vamidothion, phenthoate, dimethoate, formothion, malathon, trichlorfon, thiometon, phosmet, dichlorvos, acephate, EPBP, methylparathion, oxydemetonmethyl, ethion, salithion, cyanophos, isoxathion, pyridaphenthion, phosalone, methidathion, sulprofos, chlorfevinphos, tetrachlorvinphos, dimethylvinphos, propaphos, isofenphos, ethylthiometon, profenofos, pyraclofos, monocrotophos, azinphosmethyl, aldicarb, methomyl, thiodicarb, carbofuran, carbosulfan, benfuracarb, furathiocarb, propoxur, BPMC, MTMC, MIPC, carbaryl, pirimicarb, ethiofencarb, and fenoxycarb, pyrethroid pesticides such as permethrin, cypermethrin, deltamethrin, fenvalerate, fenpropathrin, pyrethrin, allethrin, tetramethrin, resmethrin, dimethrin, propathrin, phenothrin, prothrin, fluvalinate, cyfluthrin, cyhalothrin, flucythrinate, ethofenprox, cycloprothrin, tralomethrin, silafluofen, brofenprox, and acrinathrin, and benzoylurea and other types of pesticides such as diflubenzuron, chlorfluazuron, hexaflumuron, triflumuron, tetrabenzuron, flufenoxuron, flucycloxuron, buprofezin, pyriproxyfen, methoprene, benzoepin, diafenthiuron, acetamiprid, imidacloprid, nitenpyram, fipronil, cartap, thiocyclam, bensultap, nicotin sulfate, rotenone, mataldehyde, machine oil, and microbial pesticides e.g. BT and insect pathogenic virus.

As for the aforementioned acricides, the following can be specifically exemplified: chlorbenzilate, phenisobromolate, dicofol, amitraz, BPPS, benzomate, hexythiazox, fenbutatin oxide, polynactin, chinomethionat, CPCBS, tetradifon, avermectin, milbemectin, clofentezin, cyhexatin, pyridaben, fenpyroximate, tebufenpyrad, pylidimifen, fenothiocarb, and dienochlor. As for the aforementioned nematicides, fenamiphos, fosthiazate and the like can be specifically exemplified; as for plant-growth regulators, gibberellins (ex. gibberellin A3, gibberellin A4, and gibberellin A7), IAA, NAA, and so on can be specifically exemplified.

In the method of the present invention, when the benzimidazole-type fungicide and the other type of fungicide or the like are mixed together and used, the mixture ratio of the benzimidazole-type fungicide and the other type of fungicide or the like can vary extensively, while it ranges from 1:0.001 to 1:1000 usually, preferably it ranges from 1:0.01 to 1:100 as a weight ratio.

As for the aforementioned food crops and crops, cereals, preferably Gramineae, more preferably, wheat, barley, and the like can be exemplified. As for wheat, barley, and the like, wheat, barley, rye, oats, triticale and so on can be specifically exemplified.

The time of spraying the benzimidazole-type fungicide onto food crops depends on the types of food crops onto which the fungicides are applied and the types of disease being treated. For instance, when the benzimidazole-type fungicide is applied to wheat scab, spraying it not only in control time (GSs 49-52) but also in GS 53 to harvest time, particularly preferably spraying it at approximately the anthesis stage (GSs 60-71) can inhibit mycotoxin production effectively. Here, GS stands for growth stage of plants, which is applied by designation in the BBCH method in agriculture, representing the growth stage by a two-digit decimal system (two-digit code) from 00 to 99. This BBCH method was originally developed as a result of cooperation between public and private test and research organizations in Europe, and can be applied to all crops and weeds, and currently the extended BBCH method (The extended BBCH method, 1992, $2^{nd}$, ed. 1997) has spread to Europe and Canada mainly (see, Shokucho, vol. 36, No. 2, pp. 11-20). The aforementioned GSs are in accordance with "the extended BBCH scale (general)" on page 20 of "Shokucho".

In the method of the present invention, the amount of application of the benzimidazole-type fungicide depends on its mixture ratio with the other fungicide, weather conditions, preparation conditions, application method, location and so on, while the amount of active component usually varies from 1 to 10000 g, preferably 10 to 1000 g per 1 hectare.

The present invention includes the use of the benzimidazole-type fungicidal compound to reduce the mycotoxin content in harvested crops, and an agrichemical which contains the benzimidazole-type fungicidal compound as an active ingredient with an indication that it is used to inhibit mycotoxin production in harvested crops. The indication that it is used to inhibit mycotoxin production in harvested crops may be displayed on packaging containers or packaging bags usually, but it may be displayed in the instructions for the product.

The effectiveness of the present invention will be described by referring to the following Example, however, the present invention is not limited to this Example.

EXAMPLE

Berries of infected wheat (variety: Bandit) containing *Fusarium graminearum, Fusarium culmorum*, or *Fusarium avenaceum* were seeded as sources of inoculums of wheat scab on a farm field. When the wheat had grown to approximately anthesis stage (GSs 65 to 71), 250 g ai/ha, 375 g ai/ha, and 500 g ai/ha of the diluted thiophanate-methyl (trade name: Cercobin M) suspensions were sprayed once. Further, 500 g ai/ha of thiophanate-methyl (trade name: Cercobin M) and 120 g ai/ha of tebuconazole (trade name: Folicur) were sprayed concomitantly (wherein, ai in ai/ha is an abbreviation of "active ingredient", representing "in an active ingredient per se" or "in conversion into ingredient"). The wheat berries were sampled at harvest, the number of infected berries in 1000 berries (medicinal benefit) was studied. The quantitative analysis of deoxynivalenol (DON) was performed with an ELISA test kit from R-Biopharm AG in Germany. The results are shown in Table 1 and the FIGURE.

TABLE 1

The relationship between DON content and medicinal benefit of Cercobin M (trade name):

| Agent | g ai/ha | DON (ppb) | Medicinal Benefit* | Medicinal Benefit Control Value |
|---|---|---|---|---|
| 1 Cercobin M | 250 | 106.4 | 190 | 6.4% |
| 2 Cercobin M | 375 | 63.8 | 218 | 7.4% |
| 3 Cercobin M | 500 | 40.2 | 180 | 11.3% |
| 4 Cercobin M + Folicur | 500 + 120 | 32.7 | 78 | 61.6% |
| 5 No treatment | — | 117.1 | 203 | — |

Cercobin M: thiophanate-methyl
Folicur: tebuconazole
DON: deoxinivalenol
*Effect of controlling wheat scab: the number of infected berries in 1000 berries From Table 1 and the FIGURE, it was found that there was almost no difference in medicinal benefit (the number of infected berries in 1000 berries) between the case treated with thiophanate-methyl and the case with no treatment, while the amount of mycotoxin production (DON concentration) was inhibited in a dose-dependent manner. That is, there was no correlation observed between the effect of controlling wheat scab by thiophanate-methyl and the DON lowering effect. On the other hand, when thiophanate-methyl and tebuconazole were used concomitantly, an effect of lowering the mycotoxin production-amount (DON concentration) was observed as well as an effect of controlling wheat scab.

The invention claimed is:

1. A method for inhibiting mycotoxin production, comprising reducing mycotoxin content in harvested crops without reducing fungal infection of said harvested crops, when fungi control is incomplete, by spraying a fungicide containing a thiophanate-methyl agent as an active ingredient onto food crops.

2. The method for inhibiting mycotoxin production according to claim 1, wherein the fungicide is sprayed onto food crops during the period from their anthesis stage until their harvest.

3. The method for inhibiting mycotoxin production according to claim 1, wherein the fungicide is an admixture containing the thiophanate-methyl agent and any one of the following: a sterol biosynthesis inhibitor, a strobilurin-type agent, and a guanidine-type fungicide.

4. The method for inhibiting mycotoxin production according to claim 1, wherein the food crop is wheat, barley, rye, oats, or triticale.

* * * * *